United States Patent
Rhee et al.

(10) Patent No.: US 10,047,109 B2
(45) Date of Patent: Aug. 14, 2018

(54) ASH-FREE CYCLIC ORGANIC POLYOL-BASED REACTIVE POROGENS AND NANOPOROUS ULTRA LOW DIELECTRIC FILM BY USING THE SAME

(71) Applicant: Sogang University Research Foundation, Seoul (KR)

(72) Inventors: Hee-Woo Rhee, Seoul (KR); Sung-Min Cho, Incheon (KR)

(73) Assignee: Sogang University Research Foundation, Seoul (KR)

( * ) Notice: Subject to any disclaimer, the term of this patent is extended or adjusted under 35 U.S.C. 154(b) by 36 days.

(21) Appl. No.: 15/054,608

(22) Filed: Feb. 26, 2016

(65) Prior Publication Data
US 2016/0251381 A1   Sep. 1, 2016

(30) Foreign Application Priority Data

Feb. 27, 2015   (KR) .................. 10-2015-0028611

(51) Int. Cl.
  *C07F 7/18*  (2006.01)
  *H01L 21/02*  (2006.01)
  *H01L 23/532*  (2006.01)

(52) U.S. Cl.
  CPC ...... *C07F 7/1836* (2013.01); *H01L 21/02126* (2013.01); *H01L 21/02203* (2013.01); *H01L 21/02216* (2013.01); *H01L 21/02282* (2013.01); *H01L 23/5329* (2013.01)

(58) Field of Classification Search
  CPC ............ C07F 7/1836; H01L 21/02126; H01L 21/02203; H01L 21/02216; H01L 21/02282; H01L 23/5329
  See application file for complete search history.

(56) References Cited

U.S. PATENT DOCUMENTS

| 5,587,502 A * | 12/1996 | Moren | C07F 7/182 524/588 |
| 6,375,789 B1 * | 4/2002 | Katz | C08G 18/289 156/329 |
| 8,450,513 B2 * | 5/2013 | Chi | B82Y 30/00 556/414 |
| 2008/0237537 A1 * | 10/2008 | Huang | C07F 7/1836 252/182.3 |
| 2017/0320997 A1 * | 11/2017 | Kramer | C08G 18/289 |

FOREIGN PATENT DOCUMENTS

| KR | 20040084526 A | 10/2004 |
| KR | 10-2005-0082485 A | 8/2005 |
| KR | 10-0595526 B1 | 7/2006 |
| KR | 100672905 B1 | 1/2007 |
| KR | 20080063098 A | 7/2008 |

OTHER PUBLICATIONS

Kim, "Characterization of New Ultralow Dielectrics Fabricated by Reactive Cyclic Porogen", Sogang University, Master's Thesis, Feb. 28, 2014.
Cho et al.; "Improved Plasma Resistance of Ultralow Dielectrics by Cyclic Reactive Porogen", Proceedings The Polymer Society of Korea, Apr. 9, 2014.

* cited by examiner

*Primary Examiner* — John M Cooney
(74) *Attorney, Agent, or Firm* — Fox Rothschild LLP

(57) ABSTRACT

The present disclosure relates to a reactive porogen using cyclic organic polyol and an ultra low dielectric film prepared using the same, and more particularly, to novel cyclic organic polyol as a cyclic organic polyol compound which can be completely pyrolyzed at a temperature of 500° C. or less, does not leave carbon residue during a heat treatment if an end hydroxyl group of the cyclic organic compound is substituted by a functional group of alkylalkoxysilane and then used as a reactive porogen, and is involved in a sol-gel reaction of organic silicate and suppresses phase separation and thus forms pores having a uniform size and has excellent mechanical properties as compared with a porosity, a reactive porogen using the ash-free cyclic organic polyol, and an ultra low dielectric film prepared using the same.

4 Claims, 20 Drawing Sheets

ASH-FREE CYCLIC ORGANIC POLYOL-BASED REACTIVE POROGENS AND NANOPOROUS ULTRA LOW DIELECTRIC FILM BY USING THE SAME

CROSS-REFERENCE TO RELATED APPLICATION

This application claims the benefit under 35 USC 119(a) of Korean Patent Application No. 10-2015-0028611 filed on Feb. 27, 2015, in the Korean Intellectual Property Office, the entire disclosure of which is incorporated herein by reference for all purposes.

TECHNICAL FIELD

The present disclosure relates to a reactive porogen using cyclic organic polyol which is completely pyrolyzed without leaving carbon residue during heat treatment, a nanoporous ultra low dielectric film by prepared using the cyclic organic polyol, and a method of preparing the same.

BACKGROUND

As for system semiconductors (accounting for 80% of the semiconductor industry) represented by a micro-processor unit (MPU) of a PC and a mobile device such as a smartphone, the most important thing to secure competitiveness is a device with high integration (Moore's law), high speed of data processing, high functionalization, and low power consumption. Particularly, as the device is decreased in size, a critical dimension of an interconnect for transferring data to the outside and supplying power to a transistor is decreased, and, thus, lowering a dielectric constant (k) of an interconnect or interlayer dielectric is essential to suppress an interconnect delay or RC delay caused by the decrease of the critical dimension and also to reduce power consumption.

Low-dielectric materials may be roughly classified into inorganic materials and organic materials depending on a material, and film forming methods may be classified into a chemical vapor deposition (CVD) method and a spin-on coating method. The CVD method has the advantage of a small additional cost for equipment investment since the existing equipment can be used as it is. However, when a low dielectric film is formed by the CVD method, it is difficult to control a pore size due to random characteristics of the process. Therefore, during a next-generation device process in need of a process for an interconnect of 25 nm or less, the CVD method is less likely to decrease a dielectric constant to 2.3 or less and cannot satisfy a gap-fill characteristic, and, thus, further application thereof is uncertain. Carbon doped oxide for the CVD method may be Black Diamond II™ from Applied Materials and Aurora ULK having a dielectric constant of about 2.5, and has an elastic modulus in the range of 5 GPa to 9 GPa. Recently, the development of Black DiamondIII™ has been reported. However, it is currently known as having failed in application to a process.

Meanwhile, the spin-on method such as a nanotemplating technique developed by IBM has received attention as a method to overcome the limitation of the CVD method. The spin-on method is capable of forming a large-area film and introducing several nanometer-sized pores into the film, and, thus, can easily decrease a dielectric constant. Since the spin-on coating method can easily control a dielectric constant according to an amount of pores, it is expected to be widely used.

Representative organic porogens used to introduce pores into a film may include hyperbranched polyester [C. Nguyen, C. J. Hawker, R. D. Miller and J. L. Hedric, Macromolecules, 33, 4281 (2001)], ethylene-propylene-ethylene tri block copolymer (Pluonics™) [S. Yang, P. A. Mirau, E. K. Kin, H. J. Lee and D. W. Gidley, Chem. Mater., 13, 2762 (2001)], and polymethylmethacrylate-N,N-dimethylaminoethyl methacrylate copolymer [Q. R. Huang, W. Volksen, E. Huang, M. Toney and R. D. Miller, Chem. Mater., 14, 3676 (2002)]. However, in the case of using the above-described materials as porogens, if a porosity reaches about 15% or more due to phase separation, an interconnected pore structure is formed, which may cause a remarkable decrease in mechanical strength of a film. Therefore, in order to prepare an ultra low dielectric film having an excellent mechanical strength, it is urgent to develop a new concept porogen capable of suppressing phase separation occurring when a matrix is cured and thus minimizing a decrease in mechanical strength according to an amount of pores.

In this regard, the present inventors prepared a reactive porogen using a cyclic sugar compound, and also used the reactive porogen to prepare an ultra low dielectric film having excellent mechanical properties with an increased void content unlike conventional non-reactive porogens, such as polycaprolactone, tetronix, methyl cyclodextrin, and the like [Korean Patent Application Nos. 2004-10927 and 2004-43668]. However, as for a conventional reactive porogen using a cyclic polyol compound such as cyclodextrin and glucose, carbon residue remains even after pyrolysis during preparation of an ultra low dielectric film. Therefore, it becomes a problem when being actually applied to a semiconductor copper interconnect process.

SUMMARY

The present disclosure provides ash-free cyclic organic polyol as a cyclic organic polyol compound including a central carbocycle in which a hydrogen atom of a hydroxyl group in the central carbocycle is substituted by an alkoxysilylalkylene group, a reactive porogen using the cyclic organic polyol compound, a film forming composition including the reactive porogen, an ultra low dielectric film prepared using the composition, and a method of preparing the ultra low dielectric film.

However, problems to be solved by the present disclosure are not limited to the above-described problems. Although not described herein, other problems to be solved by the present disclosure can be clearly understood by those skilled in the art from the following descriptions.

In accordance with a first aspect of the present disclosure, there is provided a cyclic organic polyol compound including a central carbocycle in which a hydrogen atom of a hydroxyl group in the central carbocycle is substituted by an alkoxysilylalkylene group.

In accordance with a second aspect of the present disclosure, there is provided a reactive porogen the cyclic organic polyol compound according to the first aspect of the present disclosure.

In accordance with a third aspect of the present disclosure, there is provided a film forming composition including a mixture of matrix containing solution and a reactive porogen-containing solution which includes an organic silicate precursor as the matrix in the range of 10 to 90 vol %, and the porogen according to the first aspect or the second aspect of the present disclosure as a pore-forming template the range of 10 to 90 vol %.

In accordance with a fourth aspect of the present disclosure, there is provided an ultra low dielectric film, formed by a process of coating the composition according to the third aspect of the present disclosure on a substrate followed by thermal treatment.

In accordance with a fifth aspect of the present disclosure, there is provided a method of preparing an ultra low dielectric film, including: forming the film by a process of coating the composition according to the third aspect of the present disclosure on a substrate followed by thermal treatment.

According to any one of the above-described aspects, a reactive porogen designed by modifying an end of cyclic organic polyol with an alkoxysilylalkylene group so as to be directly involved in a sol-gel reaction of an organic silicate matrix suppresses aggregation of the porogen occurring at the time of phase separation caused by a chemical reaction between an end group of a matrix precursor and an alkoxysilane group of the reactive porogen, and thus shows a small and uniform pore distribution even at a high porosity, and suppresses a rapid decrease in mechanical strength caused by introduction of pores.

According to any one of the above-described aspects, a cyclic reactive porogen is completely pyrolyzed during a heat curing process. Thus, it is possible to suppress an increase in dielectric constant caused by carbon residue remaining within a film, and it is not necessary to perform an additional process, such as a UV and ozone process, for removing a non-pyrolyzed porogen.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

In the detailed description that follows, embodiments are described as illustrations only since various changes and modifications will become apparent to those skilled in the art from the following detailed description. The use of the same reference numbers in different figures indicates similar or identical items.

DETAILED DESCRIPTION

Figure 1A:
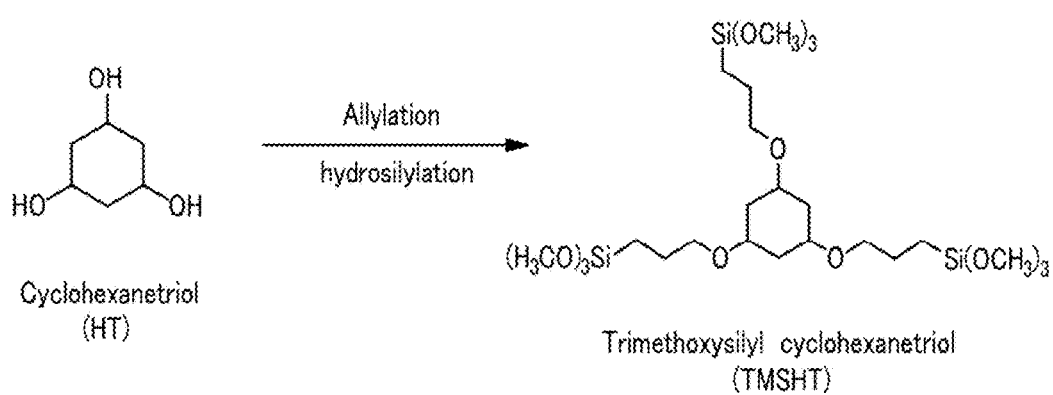
FIG. 1A and FIG. 1B are schematic diagrams showing synthesis of TMSHT and TESIT in an example of the present disclosure.

Hereinafter, examples of the present disclosure will be described in detail with reference to the accompanying drawings so that the present disclosure may be readily implemented by those skilled in the art. However, it is to be noted that the present disclosure is not limited to the examples but can be embodied in various other ways. In drawings, parts irrelevant to the description are omitted for simplicity of explanation, and like reference numerals denote like parts through the whole document.

Through the whole document, the term "connected to" or "coupled to" that is used to designate a connection or coupling of one element to another element includes both a case that an element is "directly connected or coupled to" another element and a case that an element is "electronically connected or coupled to" another element via still another element.

Through the whole document, the term "on" that is used to designate a position of one element with respect to another element includes both a case that the one element is adjacent to the another element and a case that any other element exists between these two elements.

Further, through the whole document, the term "comprises or includes" and/or "comprising or including" used in the document means that one or more other components, steps, operation and/or existence or addition of elements are not excluded in addition to the described components, steps, operation and/or elements unless context dictates otherwise.

The term "about or approximately" or "substantially" are intended to have meanings close to numerical values or ranges specified with an allowable error and intended to prevent accurate or absolute numerical values disclosed for understanding of the present disclosure from being illegally or unfairly used by any unconscionable third party.

Through the whole document, the term "step of" does not mean "step for".

Through the whole document, the term "combination of" included in Markush type description means mixture or combination of one or more components, steps, operations and/or elements selected from a group consisting of components, steps, operation and/or elements described in Markush type and thereby means that the disclosure includes one or more components, steps, operations and/or elements selected from the Markush group.

Through the whole document, a phrase in the form "A and/or B" means "A or B, or A and B".

Through the whole document, the term "alkyl group" typically refers to a linear or branched alkyl group having 1 to 20 carbon atoms, 1 to 10 carbon atoms, 1 to 8 carbon atoms, 1 to 5 carbon atoms, or 1 to 3 carbon atoms. If the alkyl group is substituted with an alkyl group, this may also be interchangeably used as "branched alkyl group". A substituent which can substitute for the alkyl group may include at least one selected from the group consisting of halo (for example, F, Cl, Br, I), haloalkyl (for example, $CCl_3$ or $CF_3$), alkoxy, alkylthio, hydroxy, carboxy (—C(O)—OH), alkyloxy carbonyl (—C(O)—O—R), alkyl carbonyloxy (—O—C(O)—R), amino (—$NH_2$), carbamoyl (—NHC(O)OR— or —O—C(O)NHR—), urea (—NH—C(O)—NHR—), and thiol (—SH), but may not be limited thereto. Further, an alkyl group having two or more carbon atoms among the above-described alkyl groups may include at least one carbon-carbon double bond or at least one carbon-carbon triple bond, but may not be limited thereto. For example, the alkyl group may include methyl, ethyl, propyl, butyl, pentyl, hexyl, hepxyl, octyl, nonyl, decyl, undecyl, dodecyl, tridecyl, tetradecyl, pentadecyl, hexadecyl, heptadecyl, octadecyl, nonadecyl, acosanyl, or all available isomers thereof, but may not be limited thereto.

Through the whole document, the term "alkoxy" refers to the above-defined alkyl group connected to an oxygen atom, and may include methoxy, ethoxy, propoxy, butoxy, pentoxy, hexyloxy, hepxyloxy, octyloxy, nonyloxy, decyloxy, undecyloxy, dodecyloxy, tridecyloxy, tetradecyloxy, pentadecyloxy, hexadecyloxy, heptadecyloxy, octadecyloxy, nonadecyloxy, acosanyloxy, or all available isomers thereof, but may not be limited thereto.

Through the whole document, the term "alkenyl group" typically refers to a monovalent hydrocarbon group including at least one carbon-carbon double bond in two or more alkyl groups among the above-described alkyl, and may include linear or branched $C_{2-20}$ alkenyl, $C_{2-10}$ alkenyl, and $C_{2-6}$ alkenyl, but may not be limited thereto. For example, the alkenyl group may include vinyl, allyl(2-propen-1-yl), 1-propen-1-yl, 2-propen-2-yl, methallyl(2-methylprop-2-en-1-yl), 2-buten-1-yl, 3-buten-1-yl, 2-penten-1-yl, 3-penten-1-yl, 4-penten-1-yl, 1-methylbut-2-en-1-yl, 2-ethylprop-2-en-1-yl, and the like, but may not be limited thereto.

Hereinafter, embodiments of the present disclosure will be described in detail. However, the present disclosure may not be limited to the following embodiments.

In a first aspect of the present disclosure, there is provided a cyclic organic polyol compound including a central carbocycle in which a hydrogen atom of (a) hydroxyl group(s) in the central carbocycle is substituted by an alkoxysilylalkylene group.

Hereinafter, in an embodiment of the present disclosure, a method of preparing a cyclic organic polyol-based reactive porogen will be described in detail. Cyclic organic polyol of the present disclosure is completely pyrolyzed at a high temperature of about 500° C. or less, and a reactive porogen combined with an alkoxysilyl alkyl group prepared using the cyclic organic polyol has a structure which can make a sol-gel reaction of an organic silicate matrix and thus can be used as a porogen template to improve mechanical properties at the same porosity.

In an embodiment of the present disclosure, polyol is a material obtained by reacting an initiator such as multifunctional alcohol or aromatic amine having two or more hydroxyl groups (—OH) or amine groups (—$NH_2$) in a molecule with propylene oxide (PO) or ethylene oxide (EO) under proper conditions, and may refer to a carbon compound having two or more hydroxyl groups, but may not be limited thereto. In an embodiment of the present disclosure, a central carbocycle of the carbon compound may be a saturated hydrocarbon cycle, an unsaturated hydrocarbon cycle, or an aromatic hydrocarbon cycle, but may not be limited thereto. For example, the central carbocycle may be a combination of a carbon atom constituting an aliphatic compound included in the polyol compound with a hydroxyl group (—OH), and may include two or more hydroxyl groups. Further, the cyclic organic polyol compound may be an organic polyol compound in which carbon atoms constituting the carbon compound form a ring or a ring being included in a molecular structure, and which is completely pyrolyzed under a heat treatment condition of about 500° C. or less, but may not be limited thereto. Particularly, if the central carbocycle of the carbon compound forms a ring, the central carbocycle may have 3 to 10 carbon atoms, but may not be limited thereto. For example, the central carbocycle may have 3 to 10, 3 to 8, 3 to 6, 3 to 4, 4 to 10, 6 to 10, or 8 to 10 carbon atoms, but may not be limited thereto. The central carbocycle may include 1 or more hydroxyl groups or 2 or more hydroxyl groups, but may not be limited thereto. For example, the central carbocycle may include 2 to 8, 3 to 8, 2 to 6, or 3 to 6 hydroxyl groups, but may not be limited thereto.

In an embodiment of the present disclosure, the cyclic organic polyol compound may be cyclohexanetriol (HT) or inositol (IT), but may not be limited thereto. For example, the cyclohexanetriol may be alicyclic hexavalent alcohol having a cyclohexane-1,3,5-hexanol structure and may be alcohol in which three of six hydrogen atoms bonded to respective carbon atoms of cyclohexane are respectively substituted by hydroxyl groups, but may not be limited thereto. Further, for example, the inositol may be alicyclic hexavalent alcohol having a cyclohexane-1,2,3,4,5,6-hexanol structure and may be alcohol in which six hydrogen atoms bonded to respective carbon atoms of cyclohexane are respectively substituted by hydroxyl groups, but may not be limited thereto. The cyclohexanetriol or inositol may be a compound which can be completely pyrolyzed under a heat treatment condition of about 500° C. or less, but may not be limited thereto.

In an embodiment of the present disclosure, there may be provided a cyclic organic polyol compound in which a hydrogen atom of a hydroxyl group in the central carbocycle is substituted by an alkoxysilylalkylene group. As a non-limited example, the alkoxysilylalkylene group may include 1 to 3 alkoxy groups, but may not be limited thereto. As a non-limited example, if the alkoxysilylalkylene group includes 1 or 2 alkoxy groups, Si included in the alkoxysilylalkylene group may be substituted by 2 alkyl groups (for example, alkyl groups having 1 to 6 carbon atoms), but may not be limited thereto. Alkylene in the alkoxysilylalkylene group may be substituted or unsubstituted $C_1$ to $C_5$ alkylene, desirably unsubstituted $C_1$ to $C_3$ alkylene, and may be, for example, ethylene, but may not be limited thereto.

In accordance with an embodiment of the present disclosure, in the cyclic organic polyol compound, a substitution reaction of a hydrogen atom of the hydroxyl group in the central carbocycle with the alkoxysilylalkylene group may be a modification of an end of cyclic organic polyol to be alkoxysilyl alkyl by consecutively performing alkenylation and hydrosilylation, but may not be limited thereto. In an embodiment of the present disclosure, the hydrogen atom of the hydroxyl group in the central carbocycle may be substituted by the alkoxysilylalkylene group, but may not be limited thereto. For example, if the substituted cyclic organic polyol compound is included in an organic silicate matrix, it may be directly involved in a sol-gel reaction with the matrix so as to form nanopores, but may not be limited thereto. To be specific, when the pores are formed, an end group of a hydroxyl group of an organic silicate matrix precursor chemically reacts with a trialkoxy group of the substituted cyclic organic polyol compound so as to suppress aggregation of the porogen occurring at the time of phase separation and thus shows a small and uniform pore distribution even at a high porosity and suppresses a rapid decrease in mechanical strength caused by introduction of pores, but the present disclosure may not be limited thereto.

In an embodiment of the present disclosure, the substituted cyclic organic polyol compound may be a compound which can be completely pyrolyzed under a heat treatment condition of about 500° C. or less, but may not be limited thereto. To be specific, the cyclic organic polyol compound in accordance with an embodiment of the present disclosure is completely pyrolyzed during a heat curing process for forming pores, and, thus, carbon residue is not formed within the pores. Further, the cyclic organic polyol compound is chemically bonded to the matrix precursor so as to have the characteristics of a reactive porogen that suppresses phase separation, and, thus, makes it possible to form an ultra low dielectric film having an excellent mechanical strength at a low dielectric constant of about 2.2 or less or about 2.0 or less through a heat curing process different from the conventional heat curing process, but may not be limited thereto.

In accordance with a second aspect of the present disclosure, there is provided a reactive porogen including the cyclic organic polyol compound according to the first aspect of the present disclosure.

Detailed descriptions of repeated parts as described in the first aspect of the present disclosure will be omitted. Although omitted in the second aspect of the present disclosure, the description of the first aspect of the present disclosure may also be applied in the same manner to the second aspect.

In an embodiment of the present disclosure, the cyclic organic polyol compound may be completely pyrolyzed under a temperature condition of about 500° C. or less without leaving carbon residue, but may not be limited thereto. For example, the cyclic organic polyol compound may be completely pyrolyzed under a temperature condition of from about 0° C. to about 500° C., from about 50° C. to about 500° C., from about 100° C. to about 500° C., from about 150° C. to about 500° C., from about 200° C. to about 500° C., from about 250° C. to about 500° C., from about 300° C. to about 500° C., from about 350° C. to about 500° C., from about 400° C. to about 500° C., or from about 450° C. to about 500° C., but may not be limited thereto.

In an embodiment of the present disclosure, a cyclic organic polyol-based reactive porogen is a compound prepared by substituting a hydroxyl group of the cyclic organic polyol compound with an alkoxysilylalkylene group by consecutively performing alkenylation and hydrosilylation. As a non-limited example, the alkoxysilylalkylene group may be 1 to 3 alkoxy groups, but may not be limited thereto. As a non-limited example, if the alkoxysilylalkylene group includes 1 or 2 alkoxy groups, Si included in the alkoxysilylalkylene group may be substituted by 2 alkyl groups (for example, alkyl groups having 1 to 6 carbon atoms), but may not be limited thereto.

In an embodiment of the present disclosure, in the alkenylation during the substitution reaction of the hydroxyl group in the cyclic organic polyol compound, the cyclic organic polyol compound is dissolved in a sodium hydroxide aqueous solution to induce a dehydrogenation reaction and then a phase separation catalyst (surfactant) and an alkenyl compound such as alkenyl halide are added to prepare a cyclic polyol derivative including an alkenyl group. The phase separation catalyst may employ alkyl ammonium halide such as tetrabutylammonium bromide, but may not be limited thereto.

The alkenyl compound may have 2 to 6 carbon atoms, but may not be limited thereto. For example, the alkenyl compound may have 2 to 5 carbon atoms, 2 to 4 carbon atoms, or 2 to 3 carbon atoms, but may not be limited thereto. For example, the alkenyl compound may include vinyl halide, allyl halide, 1-butenyl halide, 1-pentenyl halide, or 1-hexenyl halide, but may not be limited thereto.

In an embodiment of the present disclosure, the hydrosilylation during the substitution reaction of the hydroxyl group of the cyclic organic polyol compound may be performed by a reaction between the cyclic organic polyol derivative including an alkenyl group and an alkoxysilane compound in the presence of a platinum catalyst, but may not be limited thereto.

In an embodiment of the present disclosure, an alkoxy group included in the alkoxysilane compound may have 1 to 6 carbon atoms, but may not be limited thereto. For example, the alkoxy group may have 1 to 6 carbon atoms, 2 to 6 carbon atoms, or 3 to 6 carbon atoms, but may not be limited thereto.

In an embodiment of the present disclosure, if the reactive porogen including the cyclic organic polyol compound according to the first aspect of the present disclosure is included in an organic silicate matrix, it may be directly involved in a sol-gel reaction with the matrix so as to form nanopores, but may not be limited thereto. To be specific, when the pores are formed, an end group of a silanol group of an organic silicate matrix precursor chemically reacts with a trialkoxy group of the substituted cyclic organic polyol compound so as to suppress aggregation of the porogen occurring at the time of phase separation and thus shows a small and uniform pore distribution even at a high porosity and suppresses a rapid decrease in mechanical strength caused by introduction of pores, but the present disclosure may not be limited thereto. Further, the reactive porogen including the cyclic organic polyol compound does not include an oxygen atom, which causes incomplete combustion within a carbocycle unlike saccharide-based glucose (GC) and cyclodextrin (CD) having a similar structure, and, thus, can be completely pyrolyzed in a temperature range for heat curing of the matrix. Particularly, regarding phase separation, the organic silicate matrix before heat curing contains a large amount of Si—OH groups and thus has an excellent miscibility with porogens having a hydrophilic group. However, during heat curing, as a condensation reaction of the organic silicate matrix proceeds, the matrix is changed from hydrophilic to hydrophobic. Therefore, phase separation from the porogen occurs. Particularly, an increase in amount of the porogen causes a large pore and a percolated pore structure in the porogen, and a rapid decrease in mechanical property of the film. However, if the reactive porogen according to the present disclosure is included in an organic silicate matrix, the reactive porogen is directly involved in a sol-gel reaction of the matrix so as to form nanopores and thus suppresses a decrease in mechanical strength caused by introduction of pores.

In an embodiment of the present disclosure, the reactive porogen including the cyclic organic polyol compound according to the first aspect of the present disclosure may be a compound which can be completely pyrolyzed under a heat treatment condition of about 500° C. or less, but may not be limited thereto. To be specific, the reactive porogen in accordance with an embodiment of the present disclosure is completely pyrolyzed during a heat curing process for forming pores, and, thus, carbon residue is not formed within the pores. Further, the reactive porogen is chemically bonded to the matrix precursor so as to have the characteristics of a reactive porogen that suppresses phase separation, and, thus, makes it possible to form an ultra low dielectric film having an excellent mechanical strength at a low dielectric constant of about 2.2 or less or about 2.0 or less through a heat curing process different from the conventional heat curing process, but may not be limited thereto.

In accordance with a third aspect of the present disclosure, there is provided a film forming composition including a mixture of a solution containing a matrix and a solution containing the reactive porogen in which an organic silicate precursor is included as the matrix in an amount of from about 10 vol % to about 90 vol % and the porogen according to the first aspect or the second aspect of the present disclosure is included as a pore-forming template in an amount of from about 10 vol % to about 90 vol %. For example, the porogen may be included in an amount of from about 20 vol % to about 90 vol %, from about 30 vol % to about 90 vol %, from about 40 vol % to about 90 vol %, from about 50 vol % to about 90 vol %, from about 60 vol % to about 90 vol %, but may not be limited thereto.

Detailed descriptions of the repeated parts as described in the first aspect and the second aspect of the present disclosure will be omitted. Although omitted in the third aspect of the present disclosure, the description of the first aspect and second aspect of the present disclosure may also be applied in the same manner to the third aspect.

In an embodiment of the present disclosure, the organic silicate matrix may include a homopolymer or copolymer of alkyltrialkoxysilane and bis(trialkoxysilyl) alkane, but may not be limited thereto.

In an embodiment of the present disclosure, the alkoxy and alkane in the bis(trialkoxysilyl) alkane may have 1 to 6 carbon atoms, but may not be limited thereto. For example, the alkoxy and alkane may have 1 to 6 carbon atoms, 1 to 5 carbon atoms, 1 to 4 carbon atoms, 1 to 3 carbon atoms, 1 to 2 carbon atoms, 2 to 6 carbon atoms, 3 to 6 carbon atoms, 4 to 6 carbon atoms, or 5 to 6 carbon atoms, but may not be limited thereto. For example, the alkoxy and alkane may be bis(trimethoxysilyl) methane, bis(triethoxysilyl) methane, bis(trimethoxysilyl) ethane, or bis(triethoxysilyl) ethane, but may not be limited thereto.

In an embodiment of the present disclosure, the alkoxy and alkyl in the alkyltrialkoxysilane may have 1 to 6 carbon atoms, but may not be limited thereto. For example, the alkoxy and alkyl may have 1 to 6 carbon atoms, 1 to 5 carbon atoms, 1 to 4 carbon atoms, 1 to 3 carbon atoms, 1 to 2 carbon atoms, 2 to 6 carbon atoms, 3 to 6 carbon atoms, 4 to 6 carbon atoms, or 5 to 6 carbon atoms, but may not be limited thereto. For example, the alkyltrialkoxysilane may be methyltrimethoxysilane, methyltriethoxysilane, ethyltrimethoxysilane, or ethyltriethoxysilane, but may not be limited thereto.

In accordance with a fourth aspect of the present disclosure, there is provided an ultra low dielectric film formed by a process of coating the composition according to the third aspect of the present disclosure on a substrate followed by thermal treatment.

In an embodiment of the present disclosure, the ultra low dielectric film includes nanopores formed by a sol-gel reaction between the cyclic organic polyol compound and the organic silicate and does not include ash, but may not be limited thereto.

Detailed descriptions of the repeated parts as described in the third aspect of the present disclosure will be omitted. Although omitted in the fourth aspect of the present disclosure, the description of the third aspect of the present disclosure may also be applied in the same manner to the fourth aspect.

In an embodiment of the present disclosure, the ultra low dielectric film formed by a process of coating the composition according to the third aspect of the present disclosure on a substrate followed by thermal treatment includes nanopores in the film. In this case, the ultra low dielectric film may be formed by a method including forming a precursor solution by blending an organic porogen material in an organic matrix, and coating the precursor solution followed by thermal treatment, to cause nanophase separation between the porogen and the matrixso as to form a pore at a site where the porogen was located, but may not be limited thereto. Herein, the formed pores have a size of several nanometers, and the pores may be closed pores with a uniform pore size distribution, but may not be limited thereto.

In an embodiment of the present disclosure, a solution mixture may be prepared to form an ultra low dielectric film by mixing a solution containing the organic silicate matrix precursor and a solution containing the cyclic reactive porogen. Herein, the solution mixture may be prepared by mixing the solution containing the organic silicate matrix precursor in an amount of from about 10 vol % to about 90 vol % and the solution containing the cyclic organic polyol-based reactive porogen in an amount of from about 10 vol % to about 90 vol % as a pore-forming template. For example, the porogen may be included in an amount of from about 20 vol % to about 90 vol %, from about 30 vol % to about 90 vol %, from about 40 vol % to about 90 vol %, from about 50 vol % to about 90 vol %, or from about 60 vol % to about 90 vol %, but may not be limited thereto.

The prepared solution mixture may be coated on a substrate to form a film.

*61 In an embodiment of the present disclosure, as the coating method, various methods may be used. Desirably, a spin-on coating method may be used.

In an embodiment of the present disclosure, the thermal treatment may include: first curing for reacting the organic silicate matrix with the cyclic reactive porogen by inducing a chemical bond during a solvent removal and a sol-gel reaction of the organic silicate matrix under a atmosphere of nitrogen and inactive gas (Ar, etc.); second curing for increasing a curing density of the ultra low dielectric film by inducing a chemical rearrangement; and third curing for pyrolyzing the reactive porogen, but may not be limited thereto.

In accordance with a fifth aspect of the present disclosure, there is provided a method of preparing an ultra low dielectric film, including: forming a film by a process of coating the composition according to the third aspect of the present disclosure on a substrate followed by thermal treatment.

Detailed descriptions of the repeated parts as described in the third aspect of the present disclosure will be omitted. Although omitted in the fifth aspect of the present disclosure, the description of the third aspect of the present disclosure may also be applied in the same manner to the fifth aspect.

In an embodiment of the present disclosure, a temperature of the thermal treatment may be from about 0° C. to about 500° C., from about 50° C. to about 500° C., from about 100° C. to about 500° C., from about 150° C. to about 500° C., from about 200° C. to about 500° C., from about 250° C. to about 500° C., from about 300° C. to about 500° C., from about 350° C. to about 500° C., from about 400° C. to about 500° C., or from about 450° C. to about 500° C., but may not be limited thereto.

Hereinafter, the present disclosure will be explained in more detail with reference to Examples, but the following Examples are provided only for understanding of the present disclosure but not intended to limit the scope of the present disclosure.

EXAMPLE

Synthesis of Matrix

As organic silicate to be used as a precursor for an ultra low dielectric film including nanopores, an organic silicate dielectric (BTESE 25) was synthesized by copolymerizing 75 a % methyl trimethoxysilane (MTMS) and 25 mol % 1,2-bis(triethoxysilyl)ethane (BTESE). As a polymerization catalyst, a mixture of hydrochloric acid (HCl) and deionized water was used, and as a solvent, tetrahydrofuran (THF) was used. A ratio $r_1$(=mol of HCl/mol of total monomers) of the catalyst was set to 0.03 and a ratio $r_2$(=mol of $H_2O$/mol of total monomers) was set to 10.0. A reaction was carried out at a temperature of 40° C. for 6 hours to remove the HCl/$H_2O$ catalyst by extraction. The solvent was removed using an evaporator, so that a compound in the form of white powder was obtained in a vacuum. The obtained compound had a dielectric constant higher by 0.2 than a dielectric constant (k=2.7) of methylsilsesquioxane (MSSQ) but had superior mechanical properties (E=12.46 GPa, H=1.98 GPa) to MSSQ (E=4.5 GPa, H=0.7 GPa). Further, the obtained compound had an excellent thermal expansion coefficient (CTE) of 10 ppm/° C. or less.

Example 1

Synthesis of Reactive Porogen (TMSHT) using Cyclohexanetriol (HT)

Trimethoxysilylpropyl cyclohexanetriol (TMSHT) including one end substituted by a trimethoxysilyl (Si—(OCH$_3$)$_3$) group was synthesized by performing an allylation reaction and a hydrosilylation reaction to cyclohexanetriol (HT). A synthesis process of the reactive porogen was as follows. Firstly, 0.044 mol cyclohexanetriol was dissolved in 100 ml NaOH aqueous solution (33 vol %) and then, 0.0124 mol tetrabutylammonium bromide (TBAB) was added thereto as a surfactant. Then, allyl bromide adjusted to an equivalent was dropwise added thereto at regular intervals at a temperature of 40° C. to perform an allylation reaction for 24 hours. Then, surplus allyl bromide was removed, so that a material containing an allyl group was prepared. Trimethoxy silane adjusted to an equivalent was dissolved in the prepared material and then, a catalyst platinum dioxide (PtO$_2$) was added thereto to perform a hydrosilylation reaction at 90° C. Then, the solvent and the catalyst were removed, so that a reactive porogen including a trimethoxysilyl group was finally synthesized. FIG. 1A illustrated a schematic diagram of the synthesis.

Example 2

Synthesis of Reactive Porogen (TESIT) using Inositol (IT)

Figure 1B:
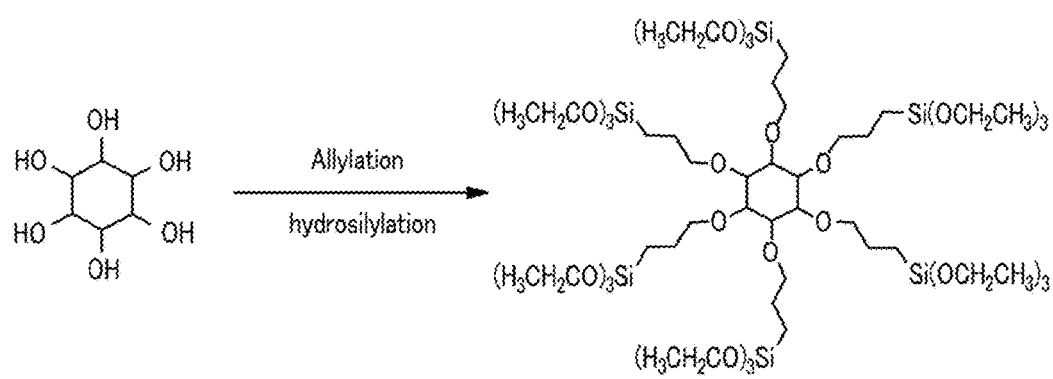

After 4.32 g inositol was dissolved in 40 ml dimethyl sulfoxide (DMSO), a resultant product was slowly put into a solution in which 9.6 g NaH was dissolved in 60 ml DMSO to induce a dehydrogenation reaction. Then, allyl bromide adjusted to an equivalent was dropwise added thereto for a predetermined period of time to perform a reaction for 4 hours. Then, the solvent and surplus allyl bromide were removed, so that inositol containing an allyl group was prepared. Trimethoxy silane adjusted to an equivalent was dissolved in the prepared inositol containing an allyl group and then, a catalyst PtO$_2$ was added thereto to perform a hydrosilylation reaction at 90° C. Then, the solvent and the catalyst were removed, so that a reactive porogen (TESIT) including a triethoxysilyl group was finally synthesized. FIG. 1B illustrated a schematic diagram of the synthesis.

Comparative Example 1

Synthesis of Reactive Porogen (TMSGC) using Glucose

Figure 11A:
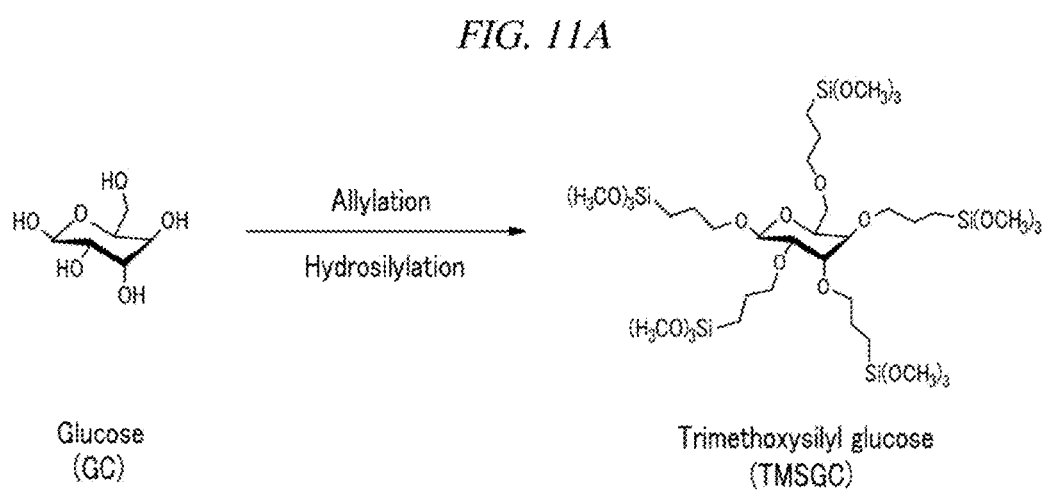
FIG. 11A and FIG. 11B are schematic diagrams showing synthesis of TMSGC and TMSCD in a comparative example of the present disclosure.

After 4.32 g glucose was dissolved in 40 ml dimethylformamide (DMF), a resultant product was slowly put into a solution in which 9.6 g NaH was dissolved in 60 ml DMF to induce a dehydrogenation reaction. Then, allyl bromide adjusted to an equivalent was dropwise added thereto to perform a reaction for 4 hours. Then, the solvent and surplus allyl bromide were removed, so that glucose containing an allyl group was prepared. Trimethoxy silane adjusted to an equivalent was dissolved in the prepared glucose containing an allyl group and then, a catalyst PtO$_2$ was added thereto to perform a hydrosilylation reaction at 90° C. Then, the solvent and the catalyst were removed, so that a reactive porogen (TMSGC) including a trimethoxysilyl group was finally synthesized. FIG. 11A illustrated a schematic diagram of the synthesis.

Comparative Example 2

Synthesis of Reactive Porogen (TMSCD) using Cyclodextrin

Figure 11B:
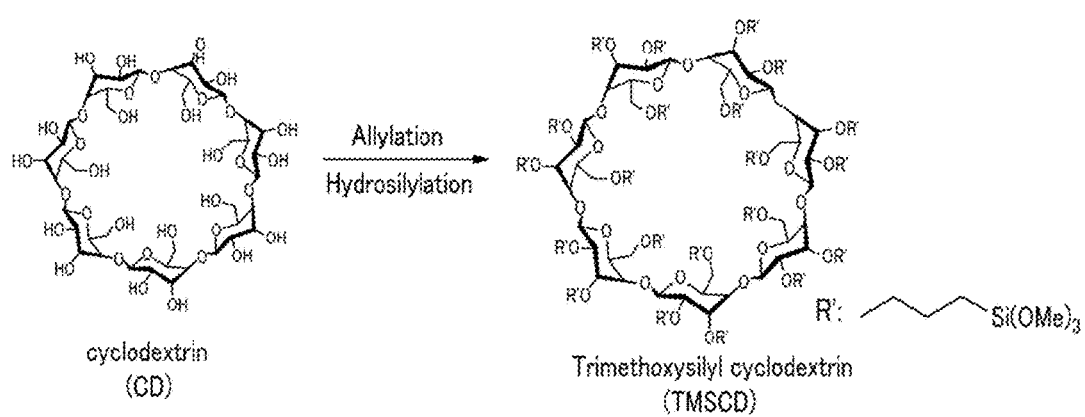

After 4.32 g cyclodextrin was dissolved in 40 ml dimethylformamide (DMF), a resultant product was slowly put into a solution in which 9.6 g NaH was dissolved in 60 ml DMF to induce a dehydrogenation reaction. Then, allyl bromide adjusted to an equivalent was dropwise added thereto to perform a reaction for 4 hours. Then, the solvent and surplus allyl bromide were removed, so that cyclodextrin containing an allyl group was prepared. Trimethoxy silane adjusted to an equivalent was dissolved in the prepared cyclodextrin containing an allyl group and then, a catalyst PtO$_2$ was added thereto to perform a hydrosilylation reaction at 90° C. Then, the solvent and the catalyst were removed, so that a reactive porogen (TMSCD) including a trimethoxysilyl group was finally synthesized. FIG. 11B illustrated a schematic diagram of the synthesis.

Trimethoxysilyl glucose (TMSGC) or trimethoxysilyl cyclodextrin (TMSCD) prepared according to Comparative Examples 1 and 2 were as shown in FIG. 11A and FIG. 11B.

Analysis Example

Preparation of Nanoporous Ultra Low Dielectric Film

Figure 2:
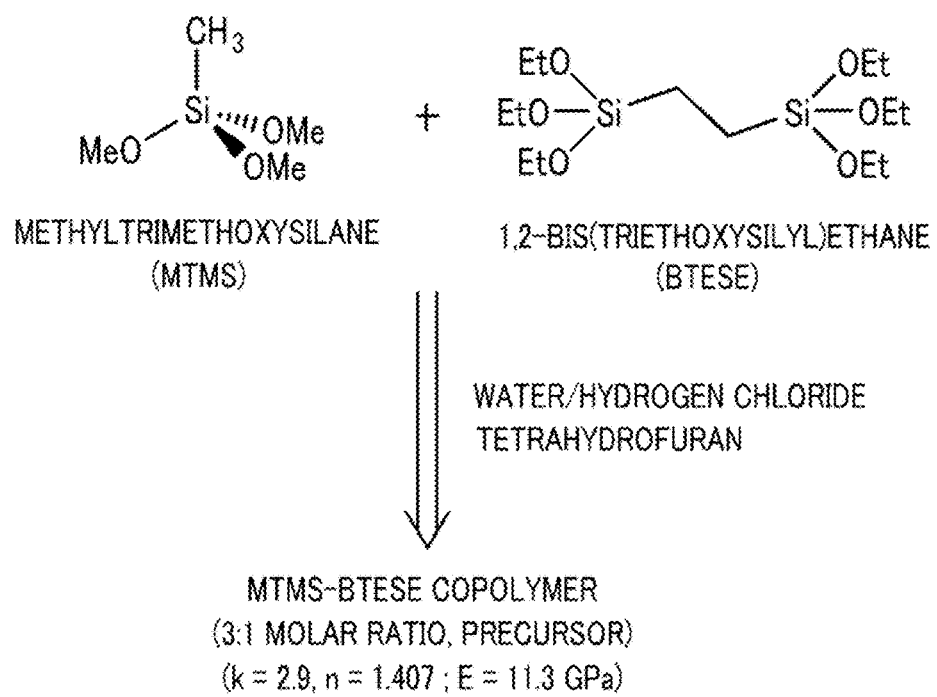
FIG. 2 is a schematic diagram illustrating an organic silicate matrix used in an embodiment of the present disclosure and a synthesis method thereof.

A process for preparing an ultra low dielectric film including nanopores using a BTESE25 copolymer as a matrix and a synthesized reactive porogen was as follows. The matrix and the porogen were dissolved in an amount of 25 wt % in propylene glycol monomethyl ether acetate, (PGMEA) as a solvent. Then, a solution mixture containing the porogen in an amount of 0 vol %, 30 vol %, 50 vol %, and 60 vol % with respect to the matrix solution was prepared. These solution was spin coated to form a film. A rotation speed was 2500 rpm and a time was fixed to 30 seconds. A temperature of the coated film was increased to 250° C. at a speed of 3° C./min and cured at 250° C. for 2 hours to induce a solvent removal, a sol-gel condensation reaction of the matrix, and a reaction between the matrix and the reactive porogen. Further, the film was heated to 300° C. at the same speed and cured at 300° C. for 2 hours to introduce pores through a spontaneous chemical rearrangement of the porogen and induce an increase in curing density of the matrix. Finally, the film was heated to 430° C. and thermally-treated at a temperature of 430° C. for 1 hour to prepare a nanoporous ultra low dielectric film. FIG. 2 is a schematic diagram illustrating a synthesis method of an organic silicate matrix.

<Characteristic Analysis>

Thermogravimetry Analysis (TGA)

In order to check thermal characteristics of a reducing sugar material selected as a porogen and whether or not the reducing sugar material was completely combusted, TGA was measured. According to the TGA, when a sample was decomposed by heat or oxidized, a weight change was measured to determine a pyrolysis temperature and a thermal behavior of the sample. The present Example was about a pyrolysis method in which only pyrolysis occurred in a nitrogen gas (N$_2$) but oxidation caused by introduction of oxygen did not occur. A temperature range was set from 40° C. to 450° C. This temperature range is required to manufacture a nanoporous ultra low dielectric. While a temperature was increased at a speed of 3° C./min, how the material was pyrolyzed was observed.

<Refractive Index (n) and Porosity (P)>

A refractive index (R.I.) of the film including nanopores was measured with a Filmetrics (F-20, Filmetrics, Inc.) with a light source having a wavelength of 632.8 nm. An average value of the refractive index was obtained by scanning 20 or more spots per sample. A porosity (P) of the nanoporous ultra low dielectric was calculated on the basis of the refractive index using Lorentz-Lorenz's formula as Equation 1 shown below.

$$\frac{n_0^2 - 1}{n_0^2 + 2}(1 - P) = \frac{n^2 - 1}{n^2 + 2} \qquad \text{(Equation 1)}$$

n$_0$: Refractive index of matrix film
n: Refractive index of porous film
P: Porosity <Dielectric Constant>

Figure 3A:
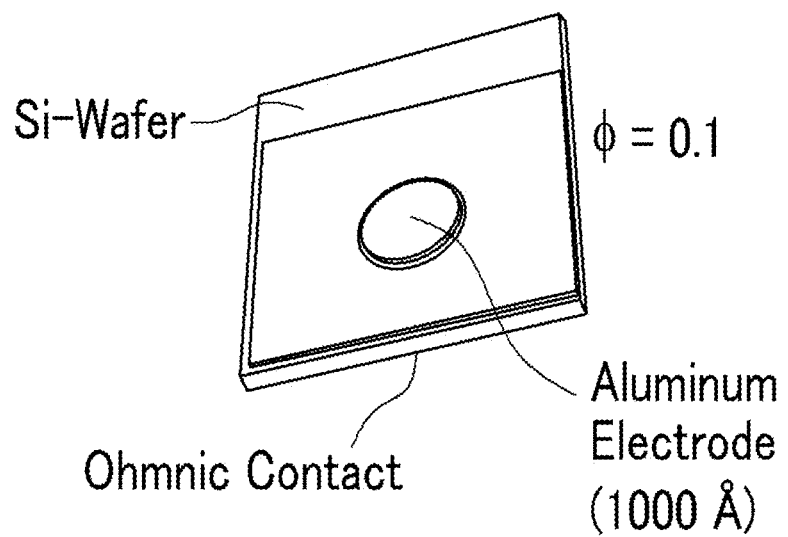
FIG. 3A and 3B are schematic diagrams illustrating a metal-insulator-semiconductor (MIS) device and a dielectric constant measurement device in an embodiment of the present disclosure.
Figure 3B:
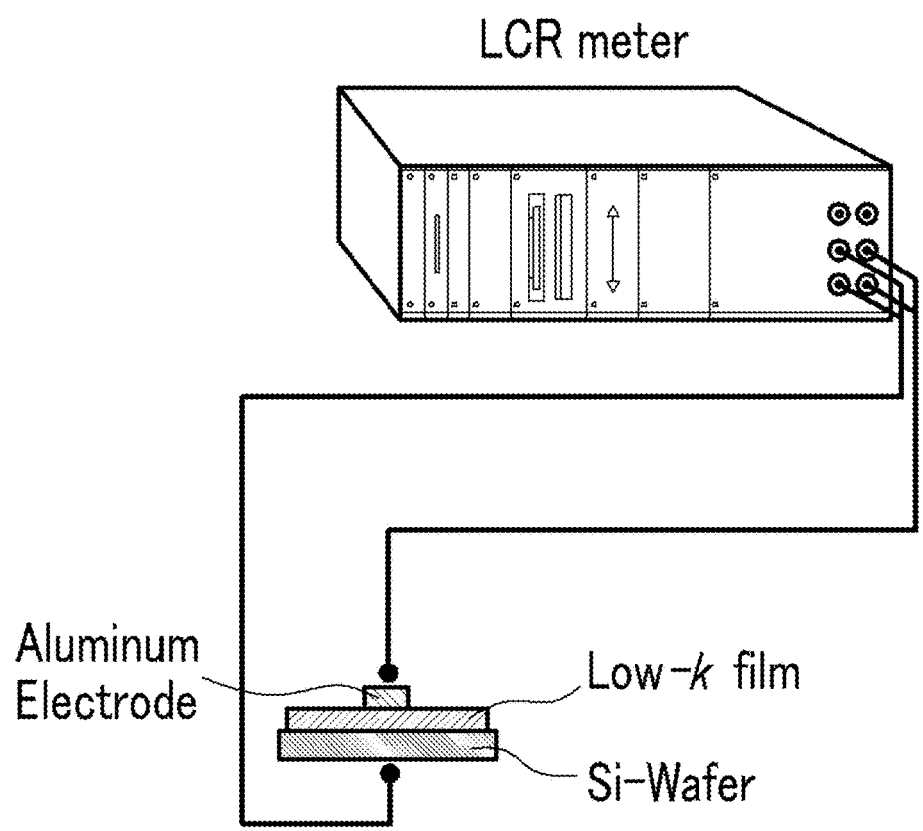

A metal-insulator-semiconductor (MIS) device was manufactured to measure a dielectric constant of the nanoporous ultra low dielectric film. The MIS device was manufactured using a lower electrode which was a Si-wafer coated with a nanoporous ultra low dielectric material and an upper electrode formed by vacuum-depositing 9 aluminum dots each having a diameter of 1 mm to a thickness of 100 nm on a cured ultra low dielectric film. The Si-wafer used as the lower electrode employed a highly doped N-type Si-wafer having a specific resistance of 0.005 Ω or less. A capacitance of the ultra low dielectric of the MIS device was measured at a frequency of 100 kHz at room temperature by using a LCR meter (Agilent, 4284A) (FIG. 3). A measurement value of the dielectric constant could be calculated by substituting the experimentally obtained capacitance in the following Equation 2.

$$k = \frac{Cd}{\epsilon_0 A} \qquad \text{(Equation 2)}$$

C: Capacitance d: Thickness of insulator plate $\epsilon_0$: Dielectric constant in vacuum A: Area of aluminum electrode <Mechanical Strength>

Figure 4:
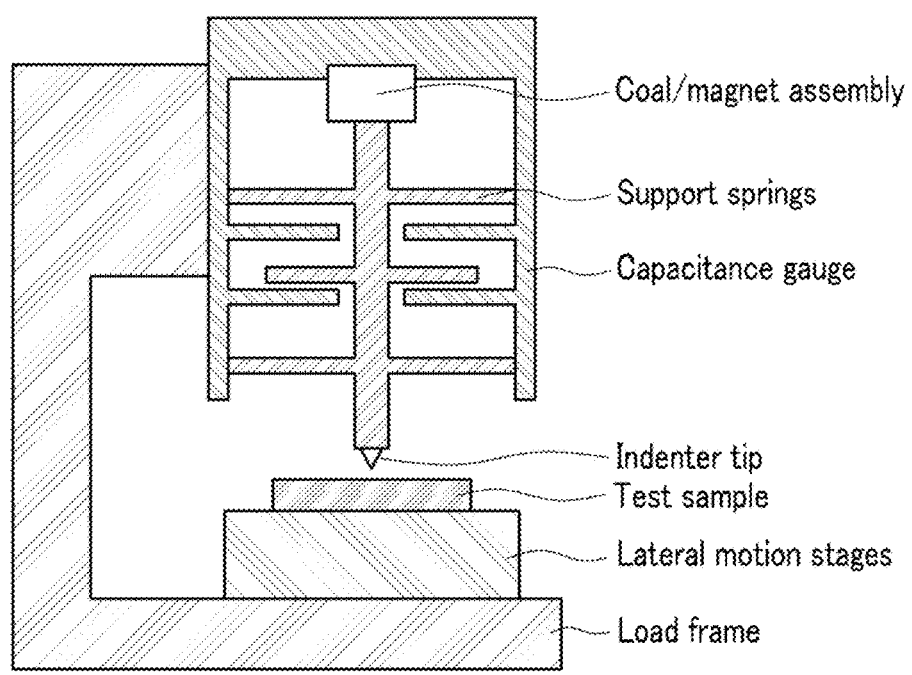
FIG. 4 is a schematic diagram of a nanoindenter in an embodiment of the present disclosure.

An elastic modulus (E) and a surface hardness (H) of the prepared film were measured through a nanoindentation (MTS XP, MTS System Corp.) test. The nanoindentation test was a method for measuring an elastic modulus and a hardness of a film by pressing a sharp indenter with a very small load to be modified to a depth of about 1 μm or less, and this test was known as one of the most useful methods for measuring mechanical properties of a film. FIG. 4 is a schematic diagram of the device. Further, with a continuous stiffness measurement function, vibration was added to an indentation depth control process so as to obtain continuous properties of a film material from a beginning of the indentation to a maximum indentation depth. Herein, an amplitude was set to be low (1 nm or 0.3 μN) not to affect an original indentation process. A measurement result distribution depending on an indentation depth was increased or decreased due to properties of a substrate material. When a property was affected by an under layer of the film and changed depending on an indentation depth, an area having a uniform property despite a change in indentation depth was measured and the measured value was generally selected as a unique property of the film. In the present Example, a Poisson's ratio was 0.24 which was obtained from an average value around 10% of a film thickness.

<Transmission Electron Microscopy (TEM)>

A surface of the nanoporous ultra low dielectric film was imaged to check sizes and distribution of pores through TEM. According to the TEM, an electron beam was accelerated at a high speed and the accelerated electron beam was irradiated to a sample to pass through a series of electromagnetic fields or electrostatic fields and then projected focusing on a fluorescent plate or a photographic to conduct an analysis. According to the TEM, an image with a high magnification of to about 1.5 million can be obtained and a microscopic structure of a sample can be seen directly.

Therefore, a shape of a several nm-sized pore can also be observed and most of structural information of the sample can be obtained.

[Analysis Result]

Figure 5:
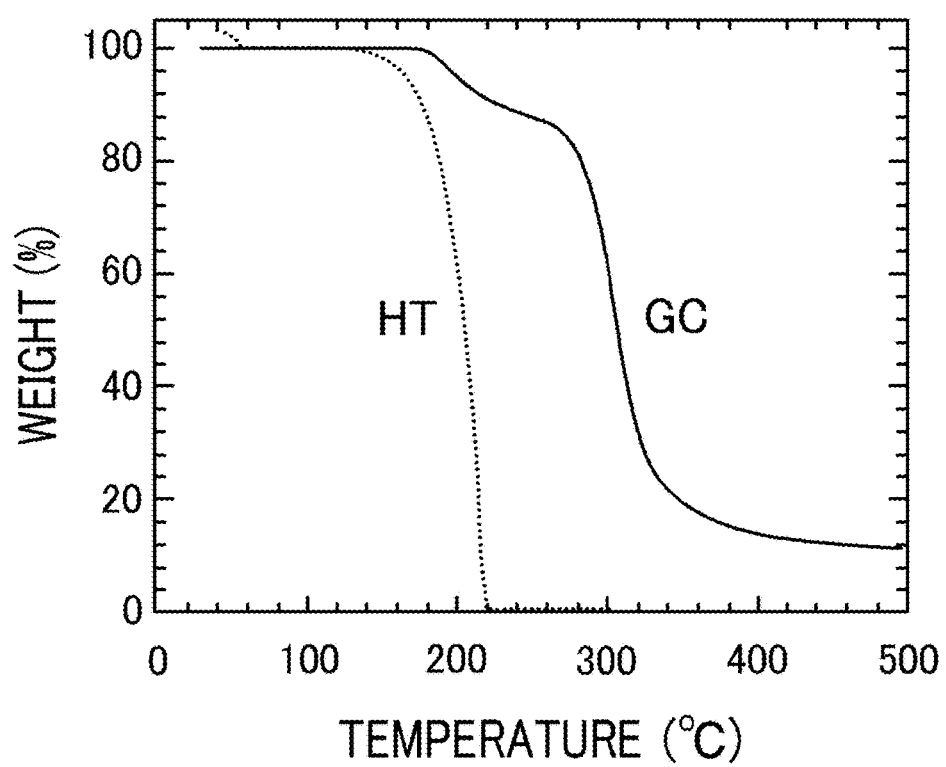
FIG. 5 is a graph comparing thermal characteristics between cyclohexanetriol (HT) and cyclic glucose (GC) used as cyclic reactive porogens in an example of the present disclosure.

In order to check a pyrolysis behavior of cyclohexanetriol (HT) as a cyclic organic polyol-based reactive porogen, TGA analysis was conducted. A porogen needs to be completely pyrolyzed without leaving ash during a heat curing process. If the porogen forms pores with ash during a heat curing process, a problem in dielectric characteristic such as a leakage current occurs, which causes an electric loss when a device operates. FIG. 5 is a graph analyzing thermal characteristics between HT and monosaccharide-based glucose (GC). As can be seen from the graph, glucose was a cyclic porogen but showed incomplete combustion due to oxygen present within a ring. Meanwhile, according to the TGA result, it was confirmed that HT had the same ring shape but was completely combusted at about 220° C. Therefore, HT has the pyrolysis characteristics suitable for a porogen of an ultra low dielectric film.

Figure 6:
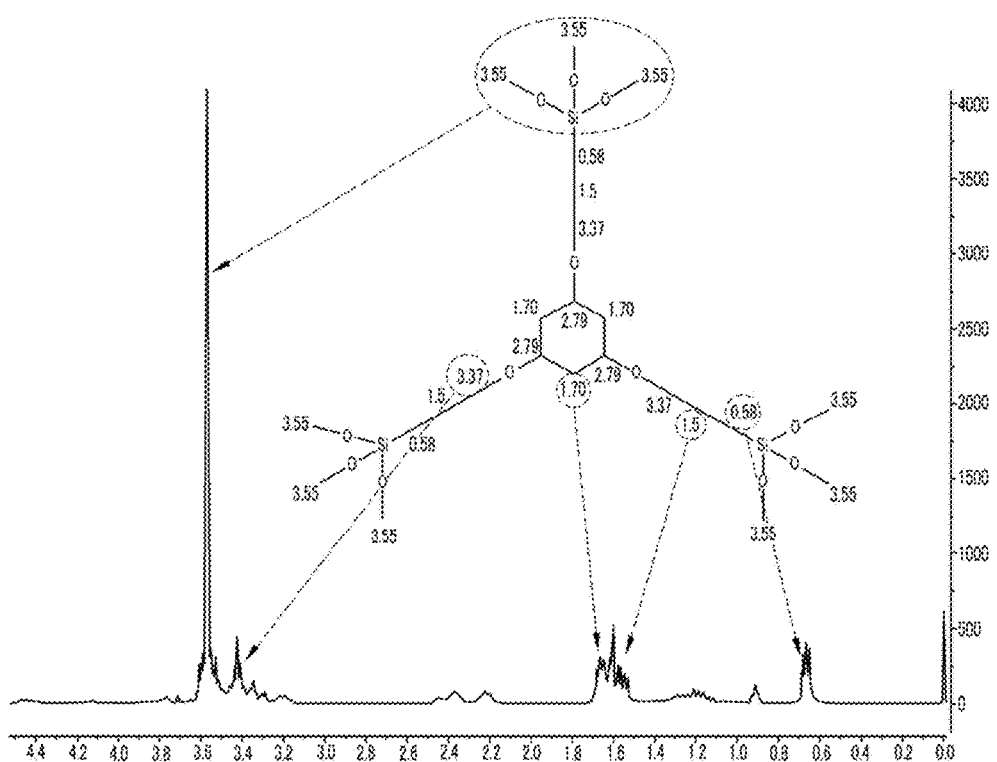
FIG. 6 shows a nuclear magnetic resonance (NMR) spectrum of TMSHT in an example of the present disclosure.

In order to check the synthesis of trimethoxysilylpropylcyclohexanetriol (TMSHT) as a newly synthesized reactive porogen, $^1$H-NMR was measured and analyzed (FIG. 6). Si—OCH$_3$ as a functional group present at an end of TMSHT was formed at 3.55 ppm, and a proton peak of a Si—CH$_2$—C bond as a product of hydrosilylation between an allyl group and trimethoxy silane was formed at about 0.58 ppm. A proton peak of a CH$_2$—CH$_2$ bond of cyclohexane as a central portion of the porogen was seen at about 1.65 ppm, and an ether bond as a product of allylation was also seen at about 3.43 ppm. It can be inferred from the above results that a new reactive porogen was synthesized well.

Figure 7:
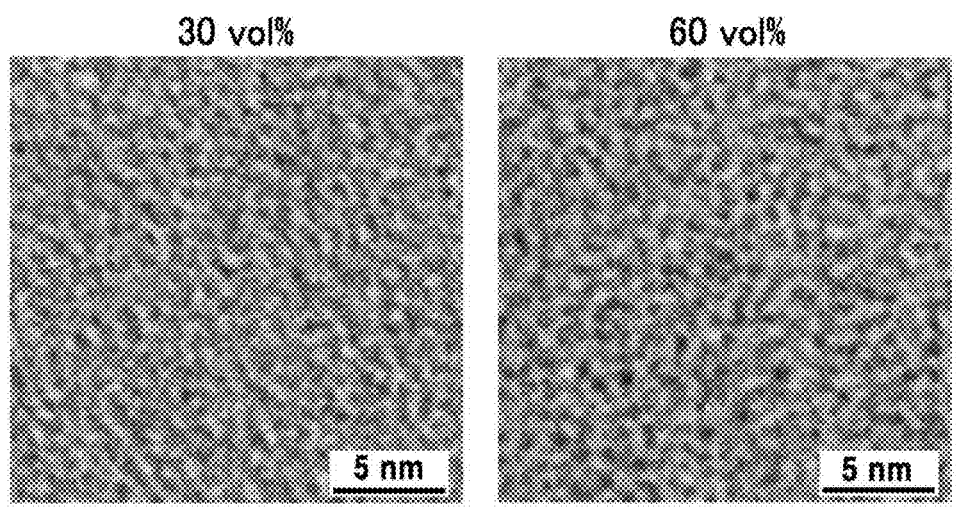
FIG. 7 shows pore images of a nanoporous ultra low dielectric film prepared by the preparation method using TMSHT depending on an amount of a porogen in an example of the present disclosure.

In order to analyze a pore size of the nanoporous ultra low dielectric film including TMSHT, a surface of the film was photographed on a nm scale using a transmission electron scanning microscope (TEM). FIG. 7 shows a result thereof. A surface of the prepared nanoporous ultra low dielectric film including TMSHT in an amount of 30 vol % and 60 vol % was photographed and measured on a 5 nm scale. A pore size was maintained at 1 nm in the ultra low dielectric including TMSHT, since aggregation of porogens does not occur due to —Si(OCH$_3$)$_3$ present at an end of a reactive porogen during a heat curing process to a matrix and the reactive porogen, and end groups of respective porogen molecules chemically react with —OH groups present in the matrix, so that pores are formed very uniformly.

Figure 8A:
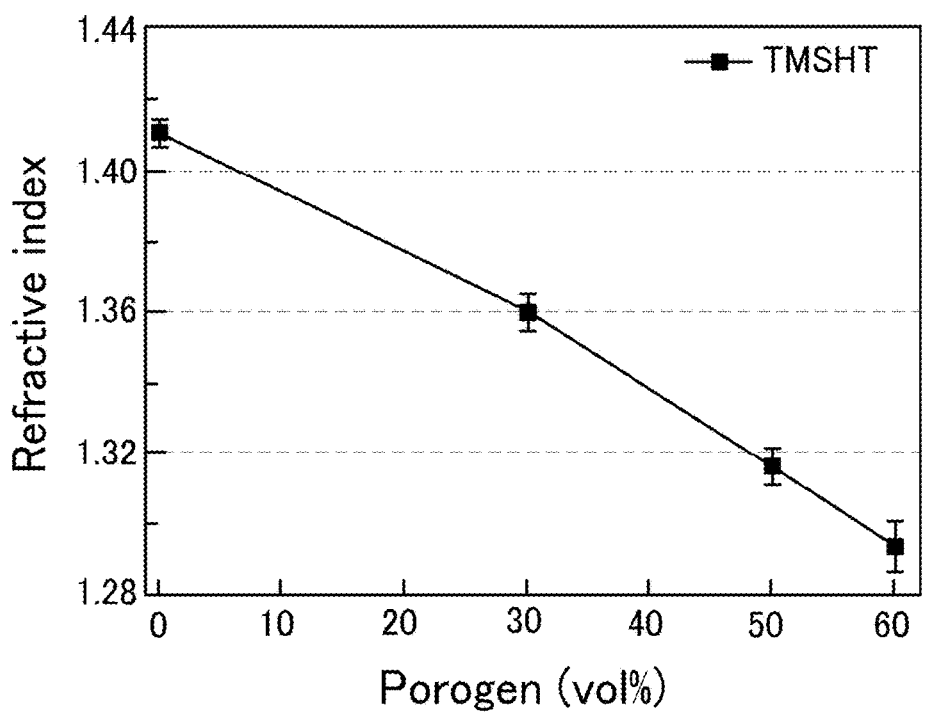
FIG. 8A and FIG. 8B are graphs respectively showing a refractive index and a porosity of an ultra low dielectric film prepared using TMSHT in an example of the present disclosure.
Figure 8B:
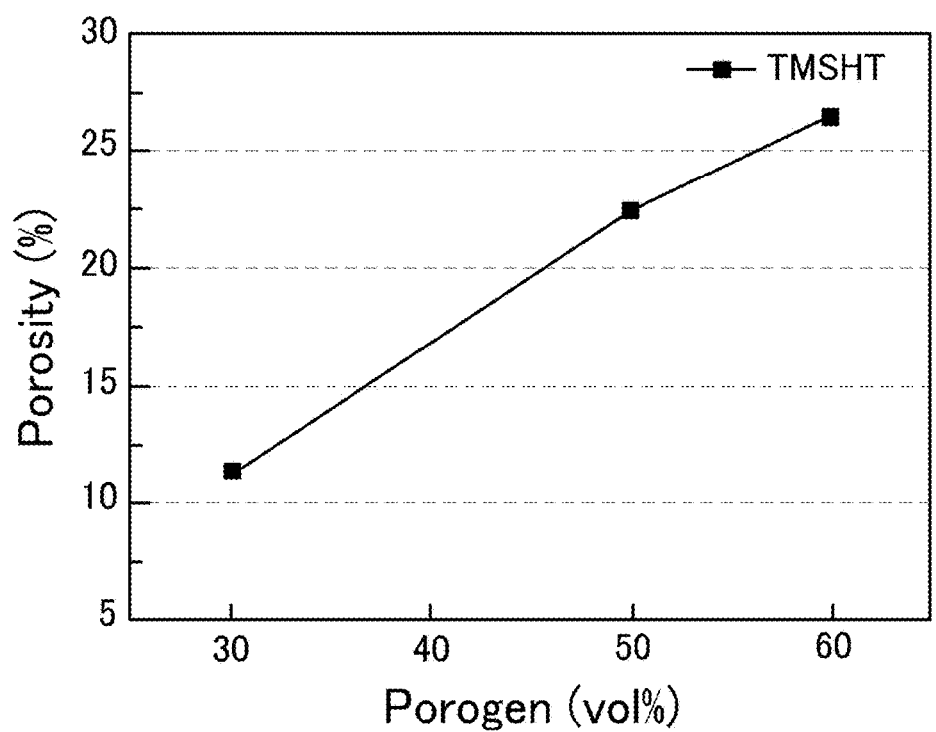

In order to compare the characteristics of the nanoporous ultra low dielectric film including the cyclic reactive porogen, reactive porogens were introduced into BTESE25 as a conventionally used organic silicate-based matrix. FIG. 8A and FIG. 8B respectively show a refractive index of an ultra low dielectric film prepared using TMSHT and a calculation result of a porosity on the basis of the refractive index.

Figure 9:
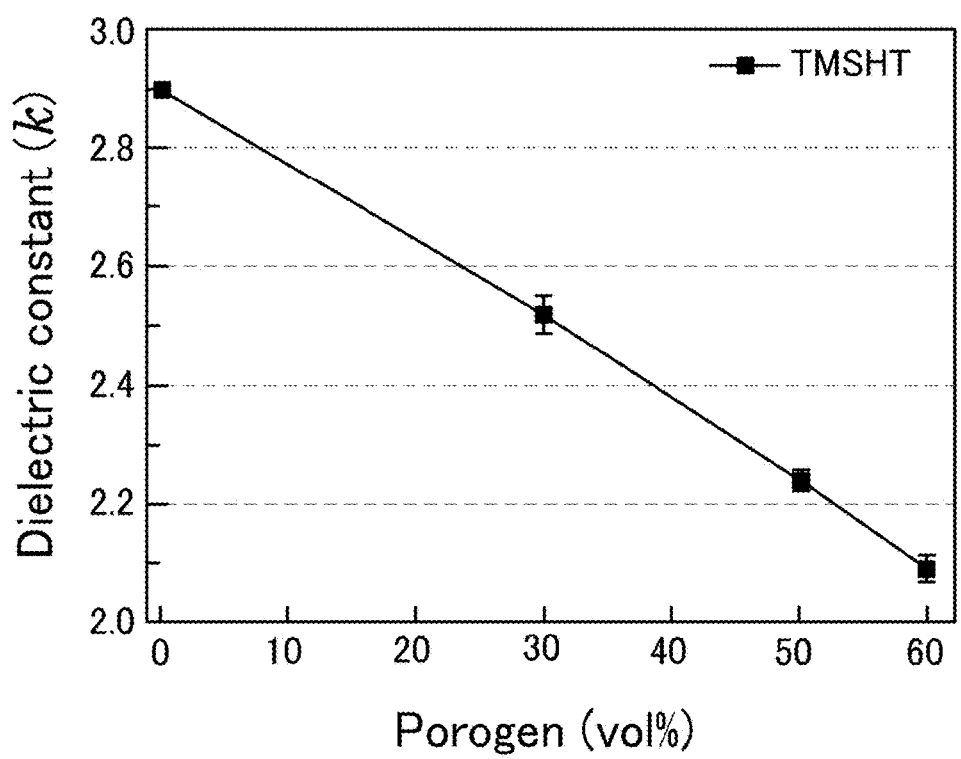
FIG. 9 is a graph showing a dielectric constant of an ultra low dielectric film prepared using TMSHT in an example of the present disclosure.

FIG. 9 is a measurement result of a dielectric constant when TMSHT is introduced into a BTESE25 matrix. When TMSHT was included in an amount of 30 vol %, a dielectric constant of the ultra low dielectric film including TMSHT was 2.52, and when TMSHT was included in an amount of 50 vol %, the dielectric constant was 2.24. When TMSHT was included in an amount of 60 vol %, the dielectric constant was 2.09 that satisfied a reference value k<2.2 for an ultra low dielectric film.

Figure 10A:
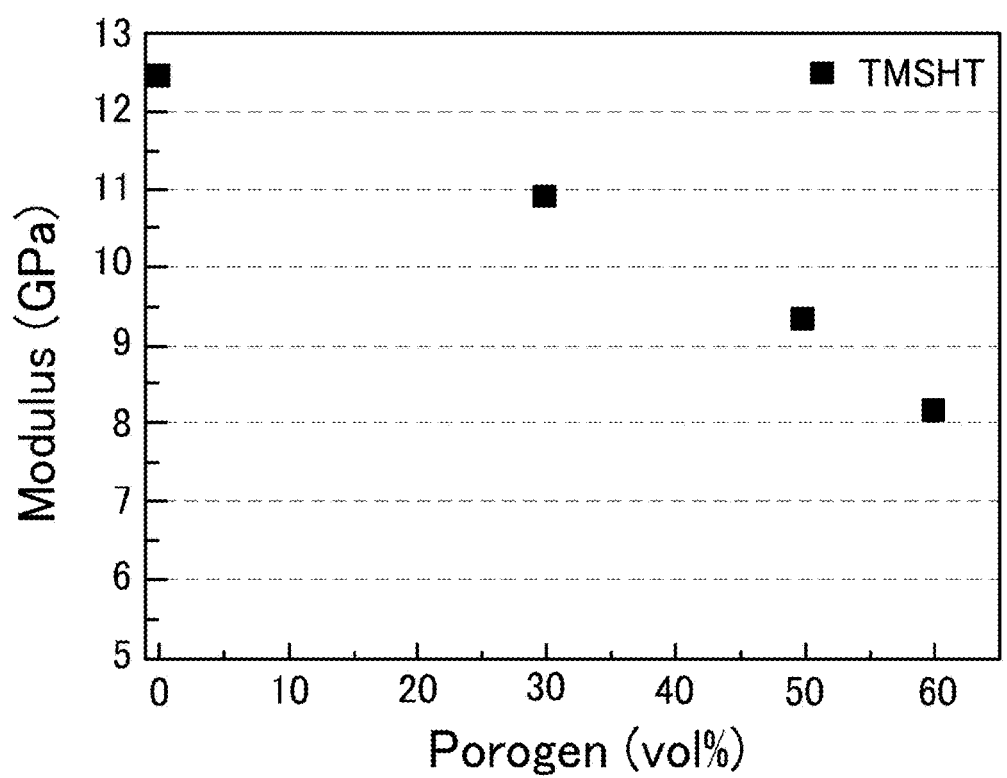
FIG. 10A and FIG. 10B are graphs showing mechanical properties of an ultra low dielectric film prepared using TMSHT in an example of the present disclosure.
Figure 10B:
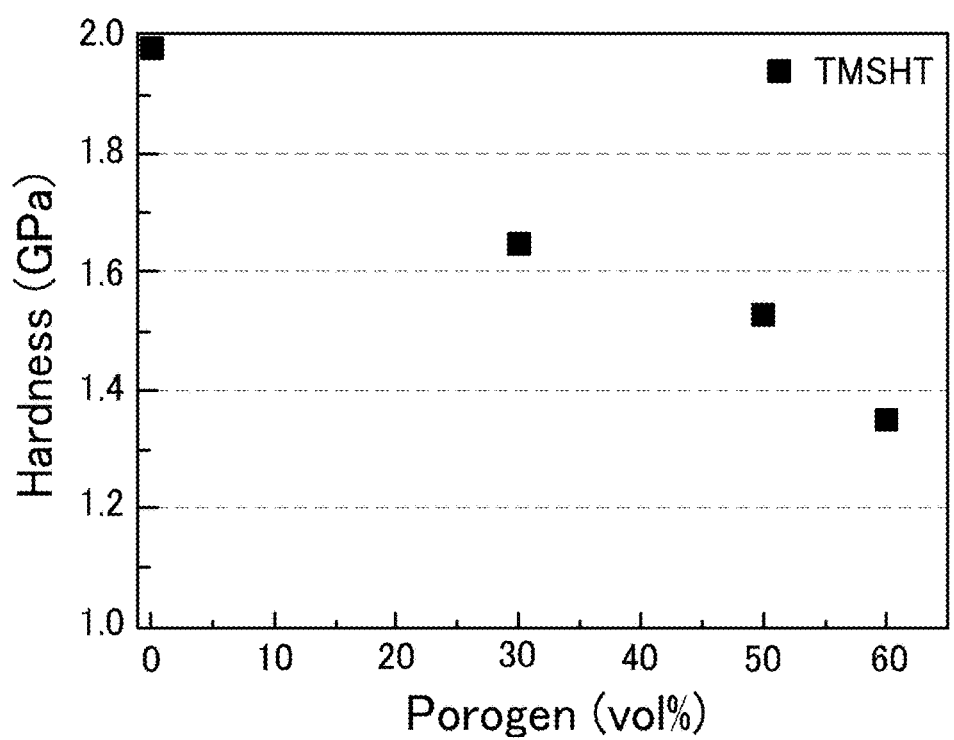

In order to check the mechanical properties of the ultra low dielectric film including TMSHT as a cyclic porogen, an elastic modulus (E) and a hardness (H) were measured. FIG. 10A and FIG. 10B are graphs showing the mechanical properties of the nanoporous ultra low dielectric film including TMSHT. A calculation was made on the basis of a result of pressing the film to a thickness of 200 nm. In order to be applied to an actual semiconductor process, the ultra low dielectric film is required to endure a CMP process, and a reference elastic modulus is 5 GPa or more and a reference hardness is 1 GPa or more. A comparison result of the mechanical strength of the ultra low dielectric film shows that an elastic modulus exceeds the reference value by 3 GPa or more and a hardness is decreased to 1.4 GPa but satisfies a level applicable to a CMP process.

According to International Technology Roadmap for Semiconductor (ITRS) 2013, an ultra low dielectric film prepared using TMSHT as a cyclic organic polyol-based reactive porogen without carbon residue has an ultra low dielectric constant (2.09) applicable to a system semiconductor process of a 11.3 nm device (until 2024) and shows a high modulus (8.15 GPa) which can endure a CMP process.

To sum up, in the present Example, an ultra low dielectric film having an excellent mechanical strength (E=8.15 GPa, H=1.4 GPa) while satisfying a low dielectric constant (k=2.09) was prepared using a cyclic organic polyol-based reactive porogen without leaving carbon residue. The above-described result shows the applicability as a next-generation semiconductor interlayer insulation material.

Figure 12:
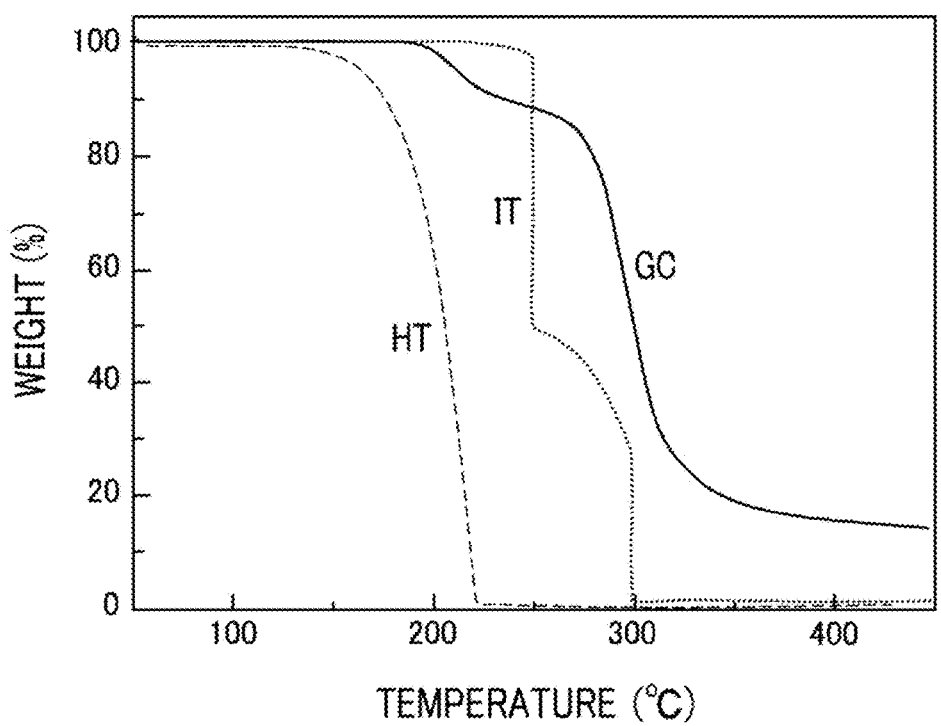
FIG. 12 is a graph comparing thermal characteristics between cyclohexanetriol (HT) and inositol (IT) used as cyclic reactive porogens in an example of the present disclosure and cyclic glucose (GC) used as a comparative example.

FIG. 12 is a graph comparing thermal characteristics between cyclohexanetriol (HT) and inositol (IT) used as a cyclic reactive porogen in an example of the present disclosure and cyclic glucose (GC) used as a comparative example. Cyclohexanetriol (HT) and inositol (IT) formed of carbon rings are completely pyrolyzed in a temperature range for a heat curing process. Meanwhile, monosaccharide-based glucose (GC) used as a comparative example is not completely pyrolyzed due to an oxygen atom in a carbon ring and thus carbon residue remains within an ultra low dielectric film, which increases a dielectric constant (k) and causes a leakage current.

Figure 13:
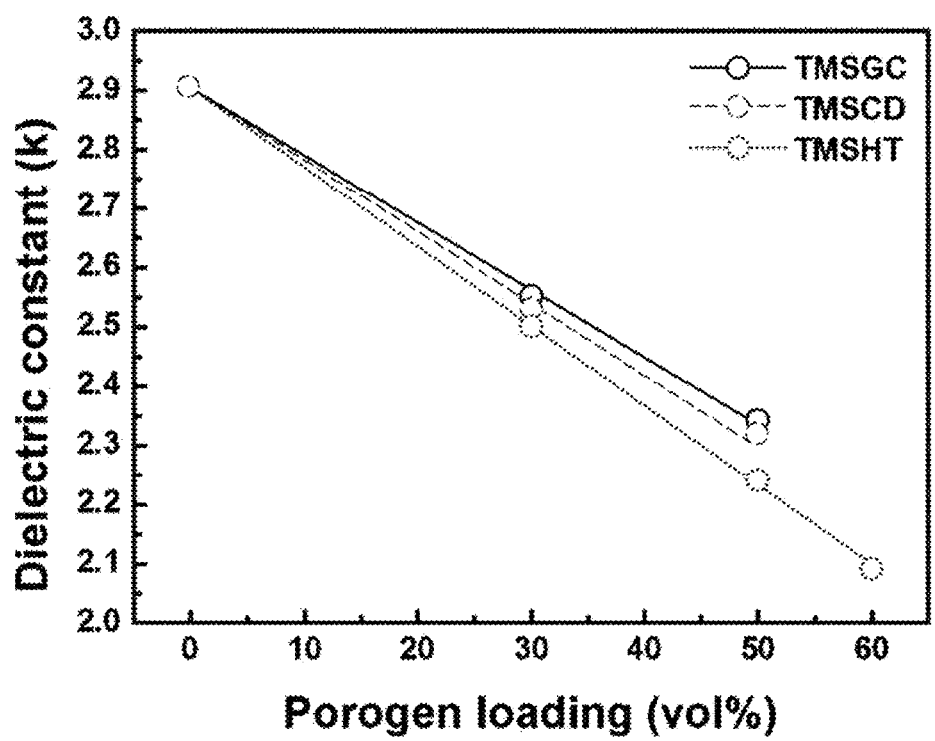
FIG. 13 is a graph comparing a change in dielectric constant depending on an amount of a porogen between TMSHT used in an example of the present disclosure and TMSGC and TMSCD used as comparative examples.

FIG. 13 is a graph comparing a change in dielectric constant of an ultra low dielectric film depending on an amount of a porogen between TMSHT used in an example of the present disclosure and, TMSGC and TMSCD used as comparative examples. In the case of using the same reactive porogen, an ultra low dielectric film prepared using TMSHT showed a lower dielectric constant than an ultra low dielectric film prepared using TMSCG or TMSCD. This is caused by thermal behaviors of HT, GC and CD. While HT is completely pyrolyzed and forms pores, GC and CD as its derivative leave carbon residue within a film and thus have higher dielectric constants than HT even at the same amount.

Figure 14:
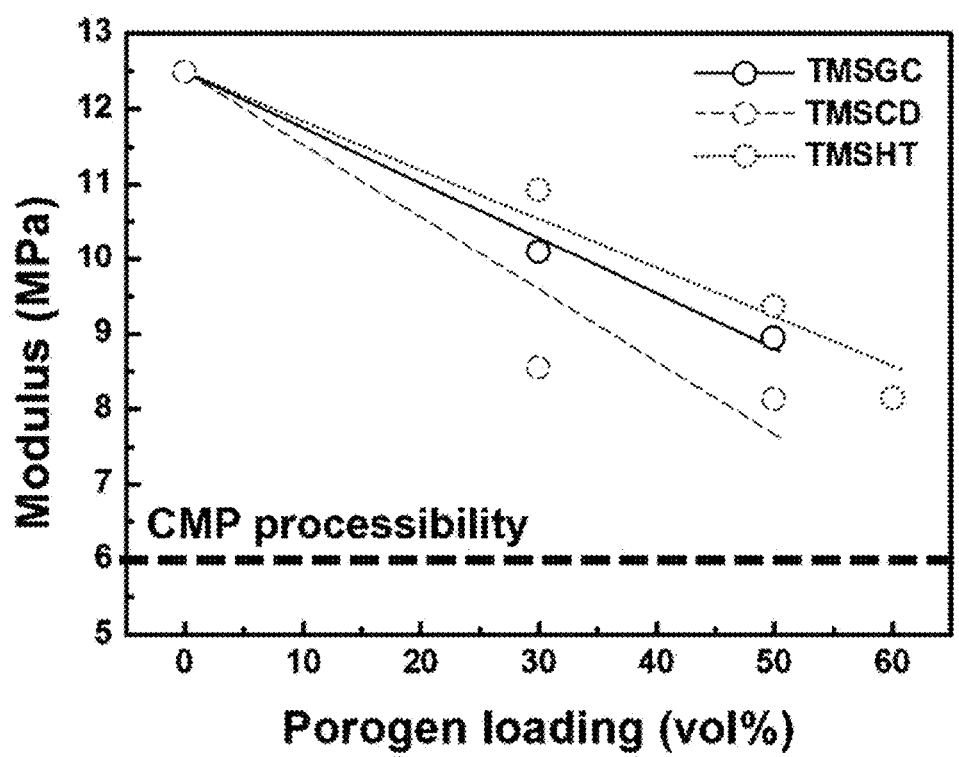
FIG. 14 is a graph comparing mechanical properties depending on an amount of a porogen between TMSHT used in an example of the present disclosure and TMSGC and TMSCD used as comparative examples.

FIG. 14 is a graph comparing mechanical properties depending on an amount of a porogen between TMSHT used in an example of the present disclosure, and TMSGC and TMSCD used as comparative examples. All of TMSHT used in an example and, TMSGC and TMSCD used as comparative examples are reactive porogens and satisfy properties applicable to a chemical-mechanical polishing (CMP) process.

Figure 15:
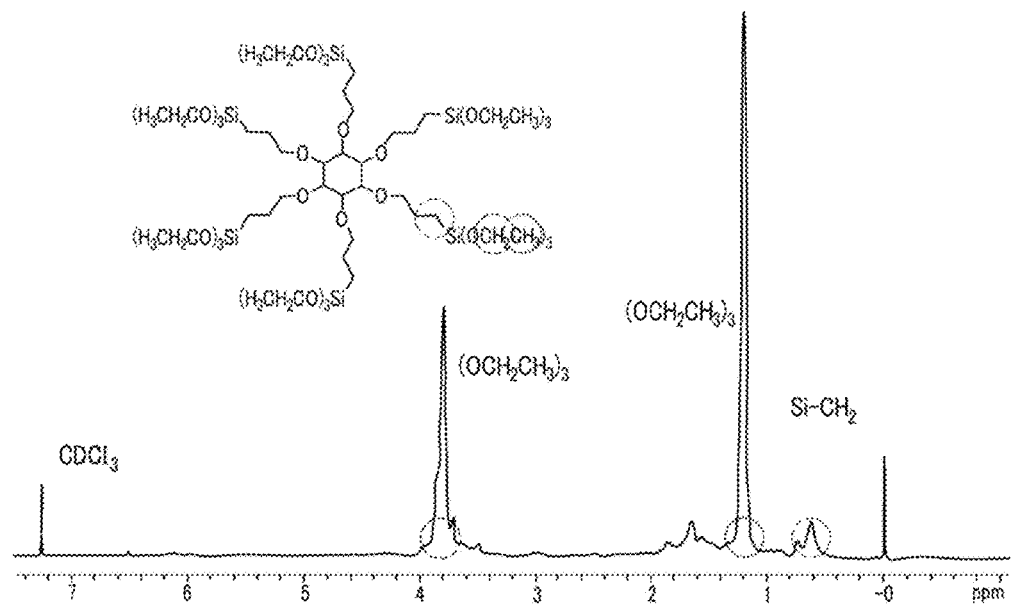
FIG. 15 shows a nuclear magnetic resonance ($^1$H-NMR) spectrum of TESIT in an example of the present disclosure.

FIG. 15 shows a nuclear magnetic resonance ($^1$H-NMR) spectrum of TESIT in an example of the present disclosure. A functional group Si—OCH$_2$CH$_3$ present at an end of TESIT was formed at about 3.55 ppm and about 1.22 ppm respectively, and a proton peak of a Si—CH$_2$—C bond as a product of hydrosilylation between an allyl group and triethoxy silane was formed at about 0.58 ppm. It can be inferred from the above results that TESIT was synthesized by allylation and hydrosilylation of inositol.

The above description of the present disclosure is provided for the purpose of illustration, and it would be understood by those skilled in the art that various changes and modifications may be made without changing technical conception and essential features of the present disclosure. Thus, it is clear that the above-described examples are illustrative in all aspects and do not limit the present disclosure. For example, each component described to be of a single type can be implemented in a distributed manner. Likewise, components described to be distributed can be implemented in a combined manner.

The scope of the present disclosure is defined by the following claims rather than by the detailed description of the embodiment. It shall be understood that all modifications and embodiments conceived from the meaning and scope of the claims and their equivalents are included in the scope of the present disclosure.

We claim:

1. A cyclic organic polyol compound comprising a central carbocycle and a plurality of hydroxyl groups, in which a hydrogen atom of each of the plurality of hydroxyl group in the central carbocycle is substituted by an alkoxysilylalkylene group, wherein the alkoxysilylalkylene group has 1 to 3 alkoxy groups, the number of carbon atoms in the alkoxy group is from 1 to 6, and the number of carbon atoms of the alkylene in the alkoxysilylalkylene group is from 1 to 5.

2. The cyclic organic polyol compound of claim 1,
Wherein the central carbocycle has 3 to 10 carbon atoms.

3. A reactive porogen comprising a cyclic organic polyol compound of claim 1.

4. The reactive porogen of claim 3,
Wherein the cyclic organic polyol compound is completely pyrolyzed at a temperature condition of 500° C. or less without leaving carbon residue.

* * * * *